United States Patent [19]
Le Menn

[11] Patent Number: 6,130,439
[45] Date of Patent: Oct. 10, 2000

[54] INSTRUMENT FOR MEASURING THE REFRACTIVE INDEX OF A FLUID

[75] Inventor: Marc Le Menn, Gouesnou, France

[73] Assignee: Delegation Generale pour l'Armement, Armees, France

[21] Appl. No.: 09/126,444

[22] Filed: Jul. 30, 1998

[30] Foreign Application Priority Data

Jul. 30, 1997 [FR] France .................................. 97 09702

[51] Int. Cl.[7] ................................................ G01N 15/06
[52] U.S. Cl. .......................................... 250/573; 356/361
[58] Field of Search .................................. 250/573, 574, 250/576, 575; 356/361, 128, 345

[56] References Cited

U.S. PATENT DOCUMENTS 4,699,951 10/1987 Allenson et al. .
5,073,024 12/1991 Valette et al. ............................ 356/361
5,151,752 9/1992 Oono et al. ............................. 356/361

*Primary Examiner*—Que T. Le
*Attorney, Agent, or Firm*—Oliff & Berridge, PLC

[57] ABSTRACT

The invention concerns in particular, an instrument for measuring the refractive index of a fluid, particularly seawater. Its object is more specifically an instrument for measuring the refractive index of a fluid having a sensor machined to contain the fluid whose refractive index is to be measured, a coherent light source which illuminates the sensor via at least one beam of coherent light, a photodetector, and processor means with which the refractive index of the fluid can be determined from the interference fringes produced by transmission and/or reflection interferences of the beam at the various optical interfaces of the sensor.

16 Claims, 8 Drawing Sheets

INSTRUMENT FOR MEASURING THE REFRACTIVE INDEX OF A FLUID

BACKGROUND OF THE INVENTION

1. Field of Invention

The present invention concerns an instrument for measuring the refractive index of a fluid, in particular of seawater.

2. Description of Related Art

At present, calculations of the physical properties of seawater are accomplished based on measurements of three variables: pressure, temperature, and conductivity. Simultaneous measurement of pressure (P), temperature (T), and conductivity (C) makes it possible to calculate salinity (S) on the basis of an international scale (Practical Salinity Scale, 1978 [PSS-78]). If the values of parameters S, T, and P are known, it is possible to calculate the specific gravity of the water ($\rho$), its specific volume ($V=1/\rho$), and its specific gravity discrepancy ($\gamma=\rho-1000$ kg/m$^3$). The value of V is then used to calculate depth and, in particular, the speed of sound.

Although measurements of P and T can be performed with sensors whose accuracy and stability are sufficient thanks to periodic recalibration, the same is not true for the parameter C, which is measured using cells which are sensitive to marine pollution. In addition, calibration of such cells is still difficult to perform. Since T and C must be measured simultaneously, response time adjustment problems may also impair the accuracy with which S can be calculated. It must also be noted that salinity is a parameter which accounts for less than 20% of any change in conductivity, and that salinity is defined in PSS-78 based on the conductivity ratio of a KCl solution and not on the basis of the conductivity ratio of a reference seawater, since the latter cannot be measured directly. The result is errors on the order of several tens of ppm in estimating the specific gravity.

Another method, known for about a hundred years, does exist for estimating directly the salinity and in particularly the specific volume of a substance. This method requires a measurement of the local, in-situ value of the optical refractive index (n). The Lorentz-Lorentz equation yields a value for n directly as a function of the specific gravity of a substance, to within 3%. Achieving greater accuracy requires calculating a polynomial which relates n to T, P, and S at a given wavelength.

The value of n varies sensitively as a function of four parameters: wavelength ($\lambda$), temperature (T), pressure (P), and concentration of solutes (NaCl, KCl, etc.), which may be called salinity (S). It is therefore necessary to know accurately the equation(s) which relate(s) these four parameters to the refractive index in order to understand how it is affected by changes in each one. Millard and Seaver have established equations which relate the index to the temperature, pressure, salinity, and density of seawater. They have shown that the polynomial equation which relates n to density is simpler than the one based on a measurement of C. This equation is at the moment less accurate, but more reliable.

The refractive index of liquids and gases is generally measured with reference to the index for air, which is known to an accuracy better than $5\times10^{-8}$ by way of the Bengt-Edlen equation. Laboratory measurements are performed using optical interferometers of Mach-Zehnder design (a variant of the Michelson interferometer), or Fabry-Perot design. Measurements in industrial or clinical contexts are also made by interferometry, using instruments that are less accurate but are portable. They can also be made using fiber-optic instruments based directly on a measurement of refractive angles.

In the laboratory, the salt concentration of seawater is measured using instruments called salinometers, which measure the conductivity of the water in question with reference to the conductivity of a reference water. While the quality of reference waters is beyond question, there can be variations between one batch and another, which impairs the reliability of the results.

Precision refractometers have been produced for making measurements at sea. U.S. Pat. No. 4,699,951, for example, describes an original method using a refractometer/salinometer which can be used at oceanographic anchorage sites, and is based on measuring the extinction of wavelengths by total reflection. Also known, from an article by Mahrt and Waldmann, is a densitometer based on a refractometry principle with which microdensity profiles can be performed very quickly to an accuracy of $1\times10^{-6}$ for n, which represents a relative uncertainty of 0.0017 kg/m$^3$ for the density. A Russian team has also created a device with which n can be measured to a relative accuracy of $1\times10^{-6}$, but this device, which is a Mach-Zehnder interferometer, is extremely bulky.

Thus, although the capabilities of these devices are interesting, the fact remains that they are large instruments which do not yield absolute measurements of refractive indices.

SUMMARY OF THE INVENTION

An aspect of the present invention is to create an instrument for measuring the refractive index of a fluid, in particular of seawater, which is very compact and accurate.

According to the invention, the instrument for measuring the refractive index comprises a sensor containing the fluid whose index is to be measured, a coherent light source which illuminates the sensor via at least one beam of coherent light, a photodetector, and a processor that determines the refractive index of the fluid from the interference fringes produced by transmission and reflection interferences of the beam at the various optical interfaces of the sensor, and wherein the sensor comprises a block of material which is transparent to the light and has a machined portion which comprises a hole or a groove and is capable of receiving the fluid, and has a surface which is flat and parallel to the hole or the groove.

According to one feature which gives access to absolute index measurements, the shape of the sensor is a cube or a parallelepiped having a bore, the axis of the latter preferably being coincident with one of the axes of symmetry of said cube or parallelepiped.

According to one feature which reduces measurement artifacts and allows refractive index measurements to be performed on a fluid under pressure, the inlet and/or outlet of the bore are machined.

BRIEF DESCRIPTION OF THE DRAWINGS

These and other objects, features, and advantages of the present invention will be set forth in detail in the description below of particular embodiments, provided in non-limiting fashion, with reference to the appended drawings in which.

DETAILED DESCRIPTION OF PREFERRED EMBODIMENTS

Figure 1:
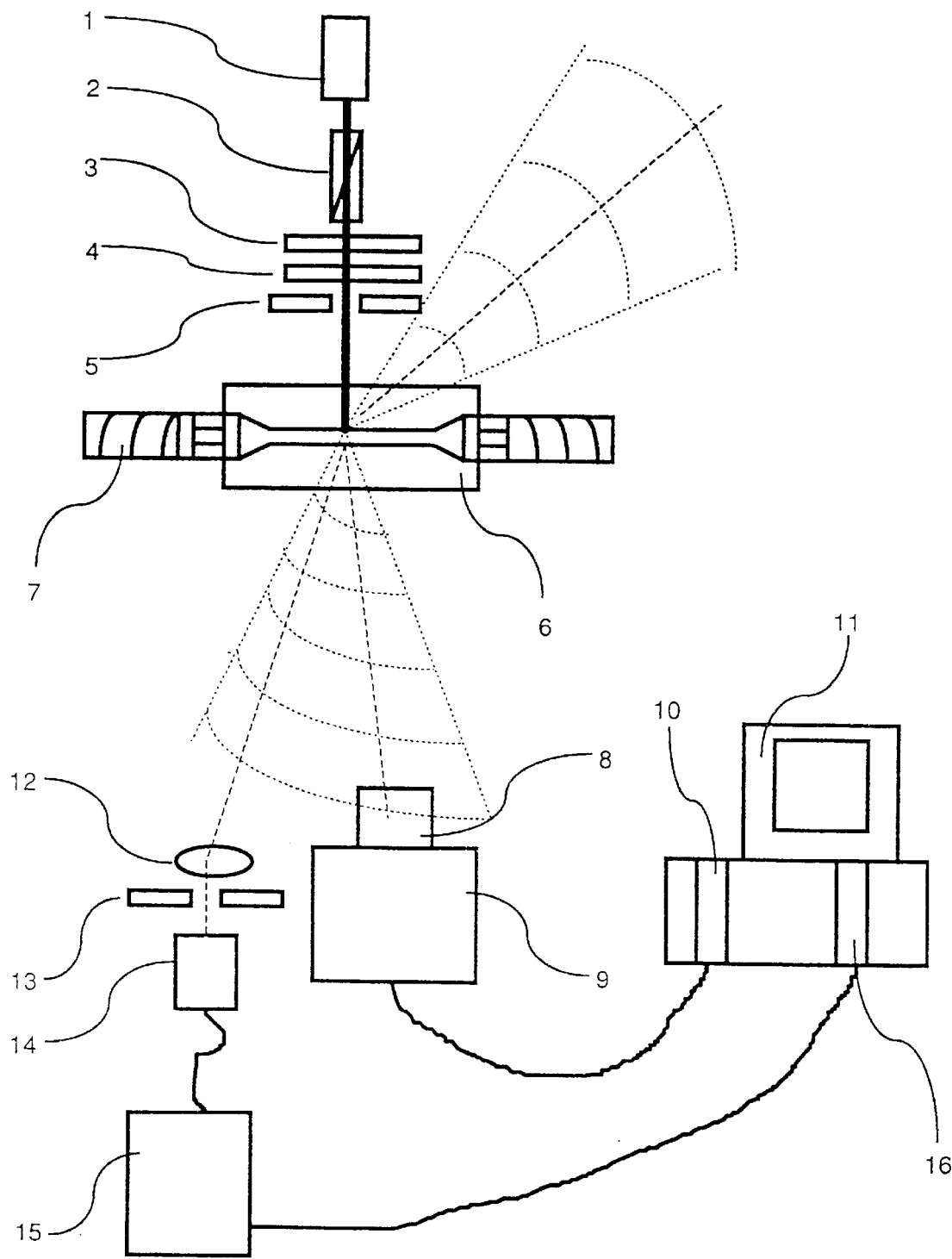
FIG. 1 shows an instrument for measuring the refractive index of a fluid using a sensor according to the invention.

FIG. 1 depicts an instrument for measuring the refractive index of seawater. The instrument has a coherent light source 1, for example a laser, which emits a beam of coherent light which illuminates sensor 6 at an arbitrary incidence. The coherent light beam is transmitted or reflected by sensor 6 toward a photoelectric detector 14. Superimposition of the rays which have traveled along different optical paths through the walls of sensor 6, by transmission and/or reflection of the beam at the various optical interfaces of sensor 6, leads to the formation of interference fringes. Photoelectric detector 14 tracks the movement of the fringes, which is a function of changes in the refractive index n of the fluid contained in or passing through sensor 6. An electronic system comprising an amplifier, an analog/digital converter, and a microcomputer processes the measurements made using the instrument.

The absolute value of the refractive index of the fluid is determined by the known method of fractional exceedances or that of coincidences, or directly by using equations which relate the index being measured to the order of the interference fringes or the interval between two consecutive fringes.

This instrument offers numerous advantages, in particular:

It is highly sensitive;
It is compact;
It is simple and inexpensive;
It can work with a circulating fluid;
It can work with small volumes of fluid;
It can determine the absolute value of the index;
A theoretical model can be used to predict the behavior of the sensor;
The sensor can be implemented using integrated micro-optical methods.

According to a particular embodiment of the instrument, a coherent light beam with a power level of 5 mW and a wavelength of 632.8 mm is emitted by a model 05 LHP 151 helium-neon laser 1 of the Melles Griot Company, for example. The beam intensity is adjusted using a Melles Griot model 03 PTA 101 Glan-Taylor polarizing prism 2, followed by a Melles Griot model 02 WRQ 023 half-wave plate 3, for example. The beam is then polarized by another half-wave plate 4, and is then spatially filtered through a Melles Griot model 04 PIP 019 circular slit 5, for example. The interference fringe images, sensed by a model MICAM VHR 1000 CCD camera 9 of the Digital Vision Technology company, equipped with a magnifying lens 8, are stored on a model IMAQ PCI-1408 circuit board 10 of the National Instrument Company, and processed using the Labview software of the National Instrument Company, for example. In parallel, a Melles Griot model 13 DSI 001 photodiode 14, preceded by a Melles Griot model 01 LAO 119 lens 12 and a Melles Griot model 04 PIP 003 circular spatial filter 13, for example, allows changes in the interference fringes to be tracked. Photodiode 14 is connected to an amplifier 15 whose output is connected to an analog-digital conversion board 16 inserted into microcomputer 11. Although specific equipment for performing aspects of the invention has been discussed above, any devices performing the functions of the invention may be used.

In a variant embodiment, the instrument can be manufactured using integrated micro-optical methods. Coherent light source 1, sensor 6, and photodetector device 14 are thus integrated onto a single substrate. The resulting instrument is then extremely compact and can be produced in large quantities at lower cost.

Figure 2:
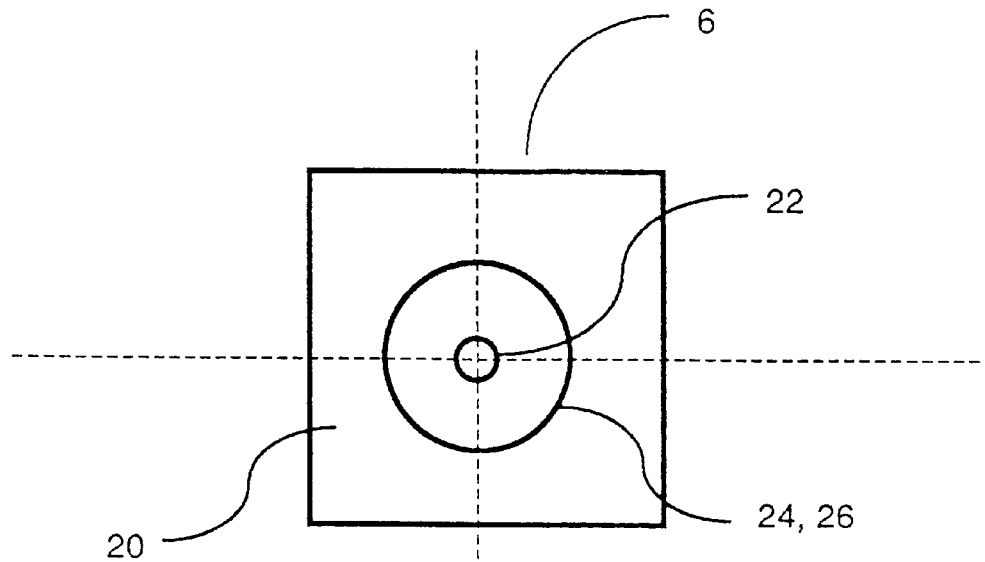
FIG. 2 shows a sensor according to the invention, viewed from above.
Figure 3:
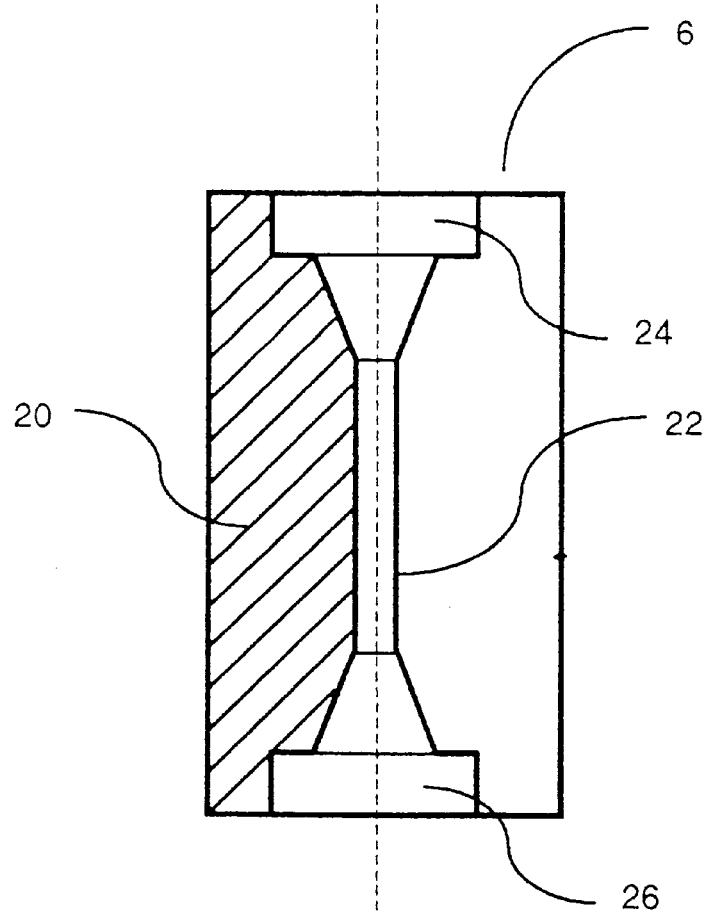
FIG. 3 shows a sensor according to the invention, viewed from the side.

FIGS. 2 and 3 depict the sensor according to the invention. Sensor 6 according to the invention is a cube or parallelepiped 20 whose center is drilled out over its entire length parallel to one of the faces. Bore 22 allows circulation of the fluid being characterized.

With this sensor shape, the mathematical expression for the resulting interferogram is particularly simple; specifically, the number of path differences causing the interference fringes is four, and the mathematical expressions for them are simple.

The sensor according to the invention thus yields absolute index measurements.

It must be noted that in the case of a capillary tube sensor, the number of path differences causing the interference fringes is very high (more than ten), and the complexity involved in processing them makes it impossible to perform direct measurements of the absolute index.

Because of its shape, a sensor according to the invention moreover possesses greater resistance to mechanical stress, which allows index measurements using a fluid under pressure. In addition, a sensor according to the invention is not subjected to changes in the temperature of the liquid, which would cause expansion of the sensor and thus a change in the measured index regardless of changes in the index of the fluid. It is thus unnecessary to work with a fluid at a quasi-constant temperature.

According to an additional feature, inlet 24 and/or outlet 26 of bore 22 can be machined for multiple uses. In one particular exemplary embodiment, inlet 24 and/or outlet 26 of bore 22 are of conical shape. This feature makes it possible on the one hand to reduce measurement artifacts and on the other hand to perform refractive index measurements on a fluid under pressure.

In the specific instance of an application as an in-situ salinity or density measurement sensor, the dimensions of the cone can be adapted to the displacement speed of the sensor or of the water mass so that the flow within the measurement orifice is laminar. The advantage of laminar flow is that it limits measurement artifacts which can be induced by turbulence.

In addition, in the case of a laboratory application, the conical shape can be utilized to attach a pressure-tight flexible connector. It is then possible to perform refractive index measurements on a fluid under pressure. In oceanography, this feature is then used to improve understanding of the equation which relates the refractive index of seawater to pressure. In this embodiment, it is also possible to calibrate and verify the response of the sensor to an applied pressure.

The sensor is manufactured from a material which is transparent to the wavelengths in use. Advantageously, said material is selected from among materials consisting of mixtures of natural quartz or silica, synthetic quartz or silica, optical glasses of the borosilicate crown or flint type, sapphire, crystalline silicon, zinc selenide, or composite ceramic glasses of the Zérodur type (Zérodur is a trademark of Schott Glass Technologies).

According to a particular embodiment of the invention, the dimensions of the sensor are adapted to the stresses associated with measuring the refractive index of seawater under pressure. Under these conditions, the index n (which varies from 1.33 to 1.36), must be measured to an accuracy of $1 \times 10^{-6}$ over a temperature range between −2 and +35 degrees C, and over a pressure range between 0 and 600 bar. A parallelepiped 20 14 mm on a side and 25.8 mm high is machined from a block of BK 7 borosilicate crown glass of Schott Glass Technologies, and a hole (bore 22) 1 mm in diameter, is bored parallel to the height. With this diameter for bore 22, it is possible to obtain a laminar flow of seawater up to a velocity of 2 m/s. Ends 24 and 26 of the drilled hole are made conical so as not only to promote flow, but also to receive model DH 1500 pressure connectors 7 of the Desgranges et Huot Company, for example. The height of the conical portion is 7.9 mm. The ends of the cones are enlarged and rendered cylindrical over a height of 4 mm to receive sealing rings of pressure connectors which convey the fluid under pressure. Lastly, the outer surfaces of the parallelepiped and the wall of the central hole are polished and rendered flat to within 0.05 $\mu$m. The outer surfaces of the parallelepiped have an antireflection coating.

Figure 4:
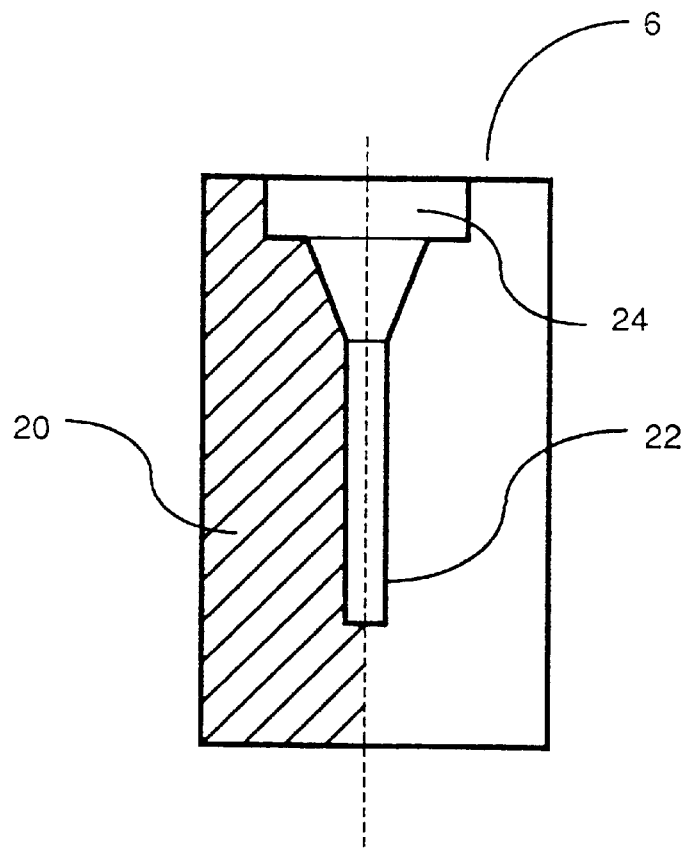
FIG. 4 shows a sensor intended for measurements on a static fluid, viewed from above.

According to a first variant embodiment depicted in FIG. 4, the parallelepiped 20 is not drilled through its entire height, so that refractive indices can be measured on a static fluid. Inlet 24 of bore 22 can be machined to receive a pressure connector 7, as above.

According to another variant embodiment, an antireflection coating is added to the sensor surface illuminated by the coherent light beam, and a coating which absorbs the reflected beam is added on the opposite surface. With this variant embodiment, it is possible to reduce the number of optical paths and thus the number of path differences which are involved in formation of the interference fringes when the sensor is being used in reflective mode. It should be noted that if the sensor 6 is illuminated at a low incidence, the interference fringes are then similar to those produced by a double-wave interferometric device.

According to another variant embodiment, the sensor 6 can be produced from a cylindrical block of glass on which the sensor surface illuminated by the coherent light beam, and the sensor surface transmitting the interference fringes, have been rendered flat.

Advantageously, a capillary tube can be inserted into the sensor bore 22 in order to reduce the bore diameter.

Figure 5:
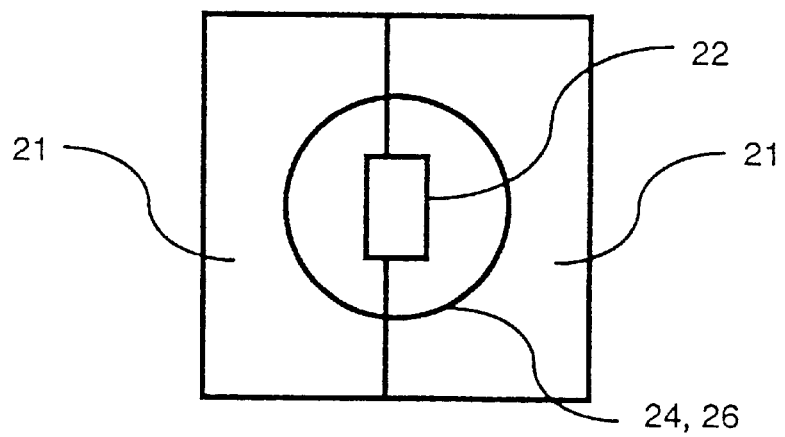
FIG. 5 shows a sensor as manufactured from two half-elements, viewed from above.

According to another variant embodiment depicted in FIG. 5, the sensor 6 is produced from two semicylindrical or parallelepipedal half-elements 21 which are assembled by optical contact or by any other adhesion method. Bore 22 can then be machined to have a rectangular shape.

Figure 11:
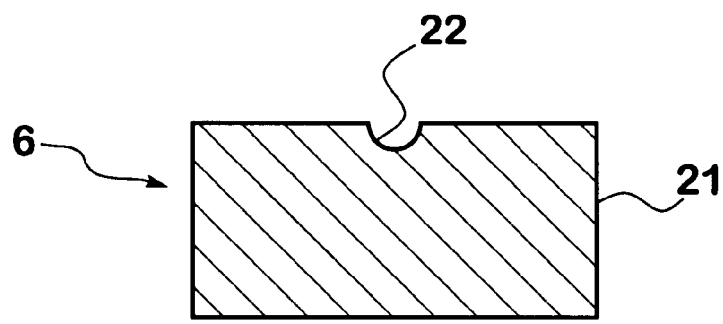
FIG. 11 shows a sensor, viewed from above, according to a variant embodiment of the invention.
Figure 12:
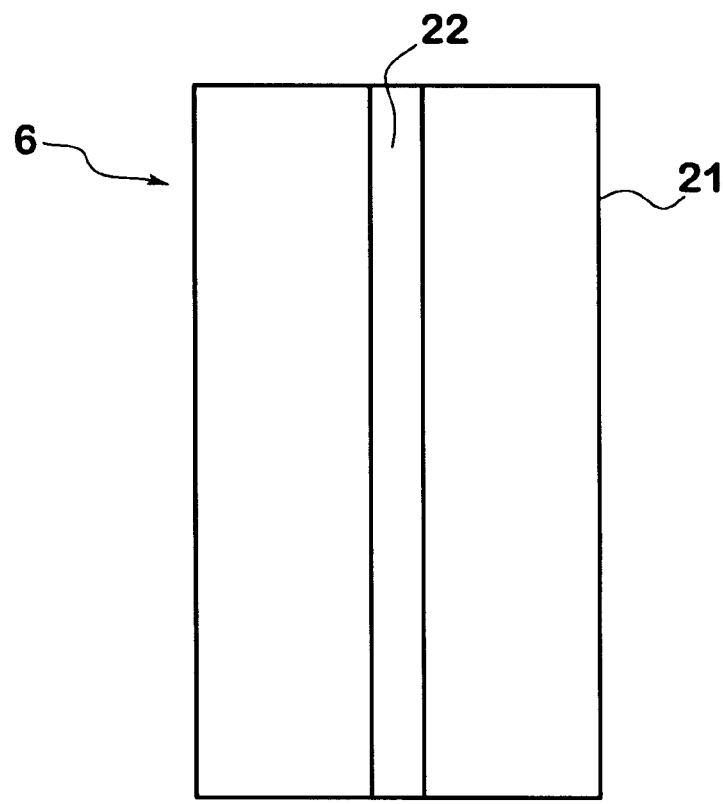
FIG. 12 shows a sensor, viewed from the side, according to the same variant embodiment of the invention.

According to another variant embodiment depicted in FIGS. 11 and 12, which eliminates any risk of clogging of the sensor bore 22 when it is being used in a fluid charged, for example, with organic matter, the sensor 6 includes only one of the two aforesaid semicylindrical or parallelepipedal half-elements 21, bore 22 having the shape of a groove, such that the groove can be, for example, U-shaped, V-shaped, or semicircular.

Figure 13:
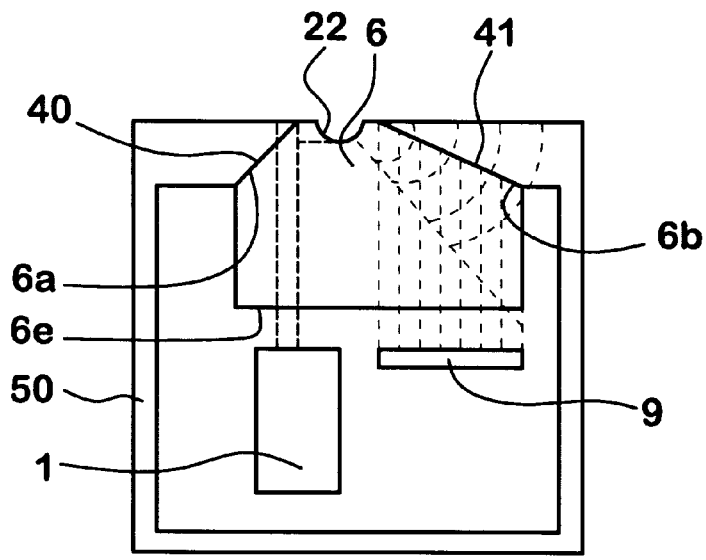
FIG. 13 shows another variant embodiment of the invention.
Figure 14:
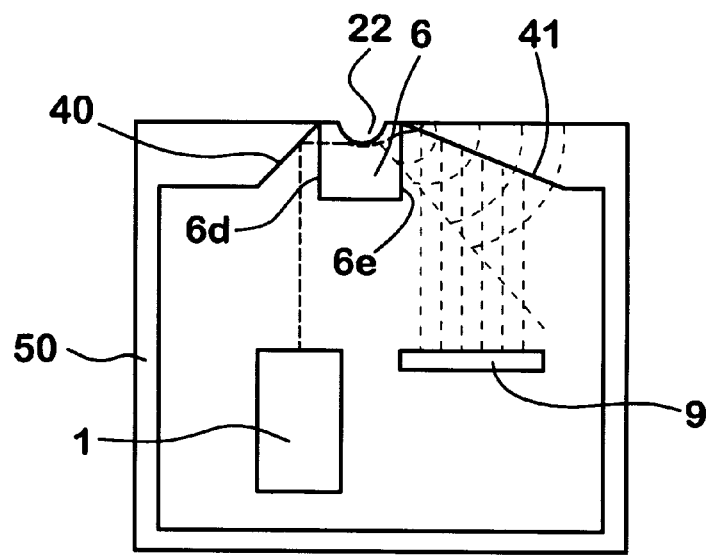
FIG. 14 shows another variant embodiment of the invention.

According to another variant embodiment depicted in FIGS. 13 and 14, mirrors 40, 41 are used to reflect, respectively in a certain direction, the beam emitted by coherent light source 1 and the interference fringes generated in the sensor 6.

In FIG. 13, mirrors 40 and 41 are attached to two beveled surfaces 6a and 6b of the sensor. The beam emitted by coherent source 1 enters the sensor 6 through its flat surface 6c parallel to groove 22. It is then reflected by mirror 40 in the direction in which interference fringes are formed during interaction between the groove and the beam. The fringes are then reflected by mirror 41 toward photodetector 9, and emerge from the sensor 6 through its surface 6c.

Source 1, detector 9, and a portion of sensor 6 are arranged inside a sealed casing 50.

It can be noted that in this variant embodiment, the sensor 6 requires the use of only a single surface that is flat and parallel to groove 22.

In FIG. 14, mirrors 40 and 41 are arranged on either side of sensor 6. The beam emitted by coherent source 1 is directed toward mirror 40. It is reflected by the latter, and enters the sensor through its flat surface 6d parallel to groove 22. The interference fringes formed during interaction between the groove and the beam are in turn reflected by mirror 41 toward photodetector 9.

As above, source 1, detector 9, and a portion of the detector are arranged inside a sealed casing 50.

Figure 6:
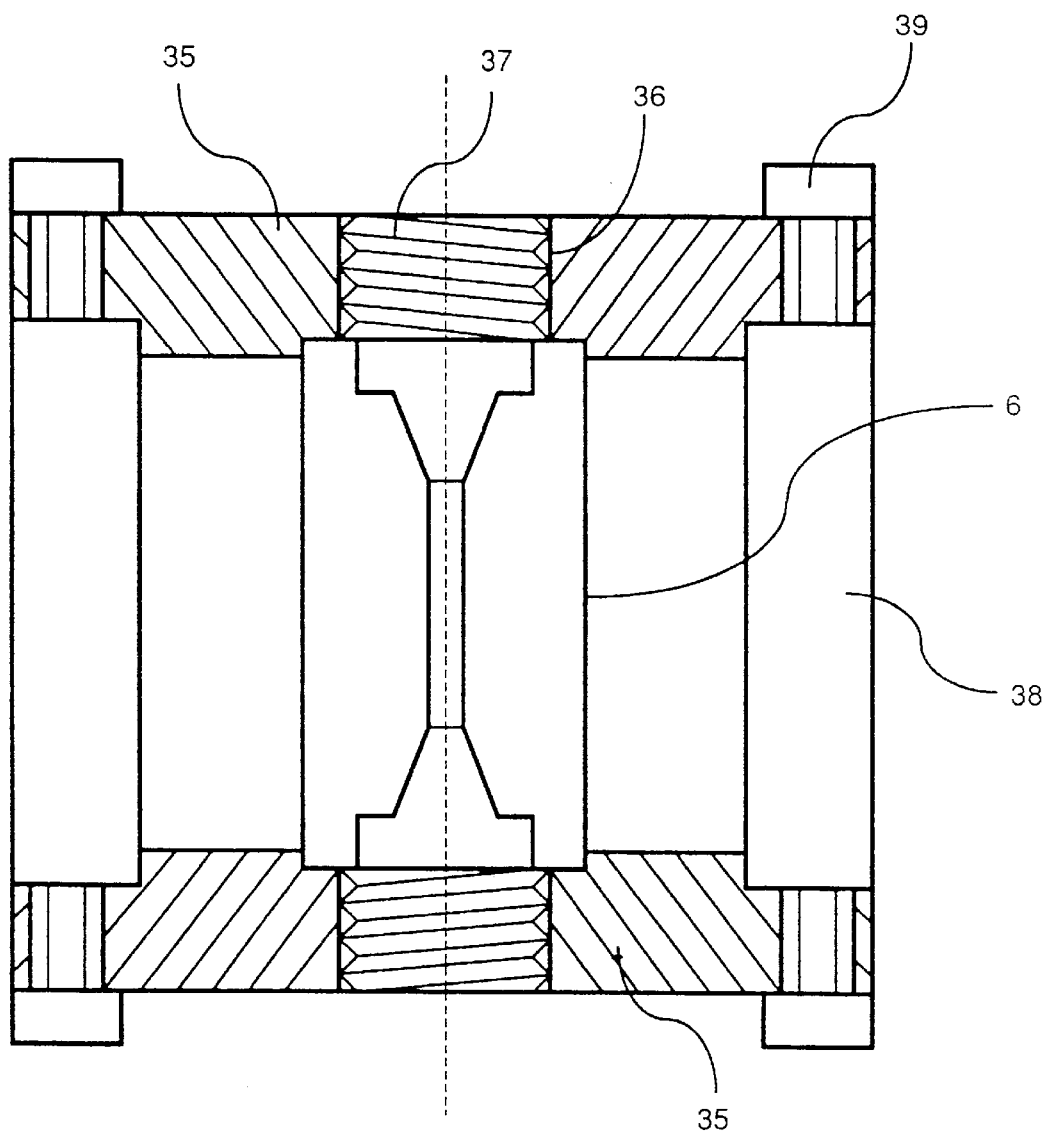
FIG. 6 shows a sensor and mounting flanges for pressure connectors, viewed from the side.

According to another variant embodiment depicted in FIG. 6, pressure connectors 7 can be retained on the sensor by two flanges 35. Flanges 35 are equipped with steps 36 into which sensor 6 is recessed. The flanges are drilled and threaded in the alignment axis of the sensor 6 and the pressure connectors 7. Pressure connectors 7 are screwed onto the flanges by means of threads 37. The two flanges are assembled and coupled via guides 38 and screw-nut assemblies 39.

Figure 7:
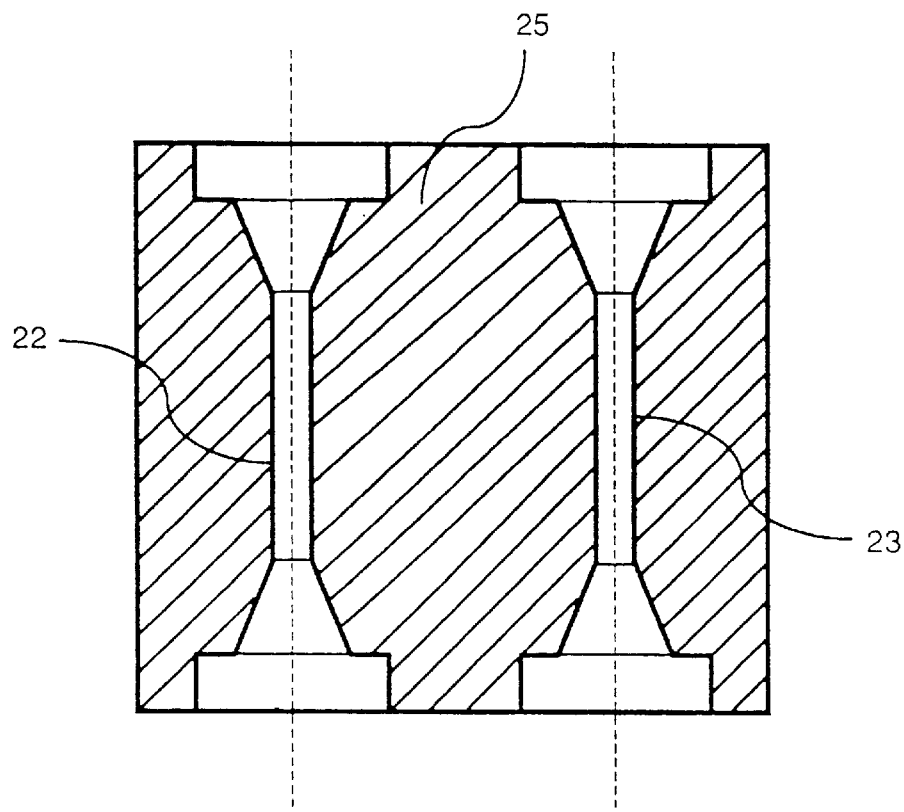
FIG. 7 shows a double sensor with which differential measurements can be made, viewed from the side.

According to another variant embodiment depicted in FIG. 7, the sensor 6 has two parallel holes 22 and 23. The first hole 22 and second hole 23 contain respectively, a reference fluid whose refractive index and changes in refractive index are known, and a fluid whose index and changes in index are to be determined with reference to the reference fluid. If it is desirable for the temperature of the two conduits to be homogeneous, the two holes 22 and 23 are then produced in a single block of glass 25. If the two fluids must be investigated at different temperatures, the two holes 22 and 23 are then produced in different blocks of glass 20. These two types of sensors 6 can also be used to measure relative changes in index between two fluids whose refractive indices are unknown. The coherent light can derive from a single source, and can be separated into two beams by known separation methods.

Figure 8:
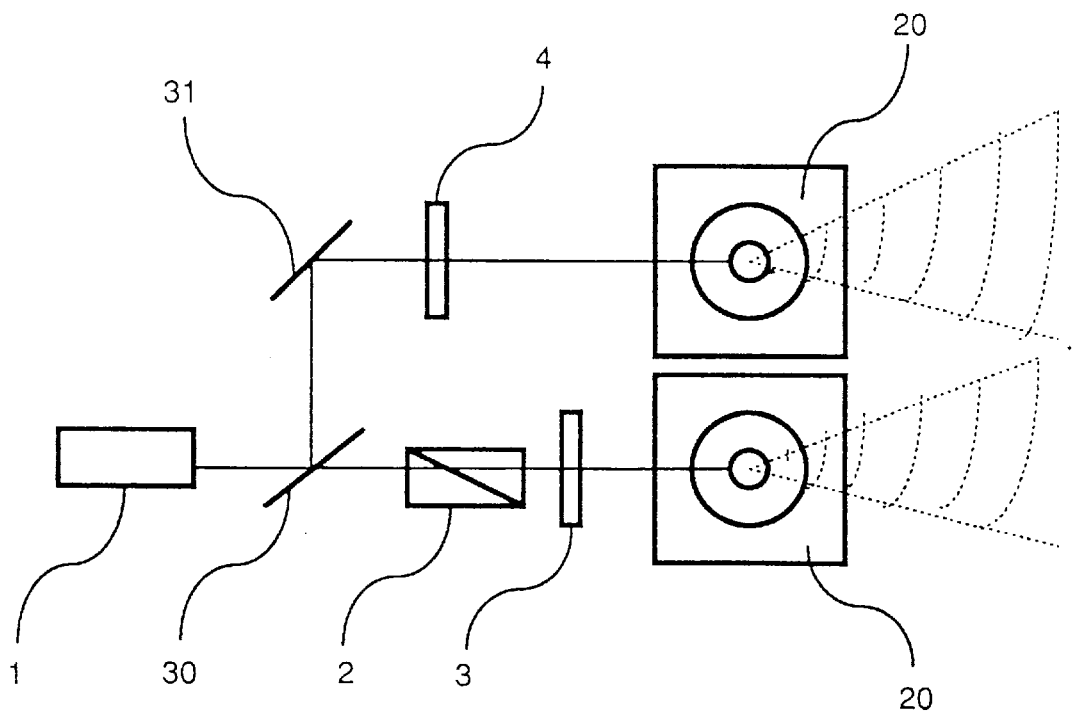
FIG. 8 shows an instrument for differential measurement of the refractive index of a fluid, using a semi-reflective plate and a sensor according to the invention, viewed from above.

FIG. 8 depicts an instrument for differential measurement of the refractive index of a fluid using a linearly polarized coherent light source 1. A semi-reflective plate 30 is used to separate the beam into two. The second beam is then sent toward the second sensor via a beam-folding minor 31, and a half-wave plate 4 makes it possible to adjust its phase angle.

Figure 9:
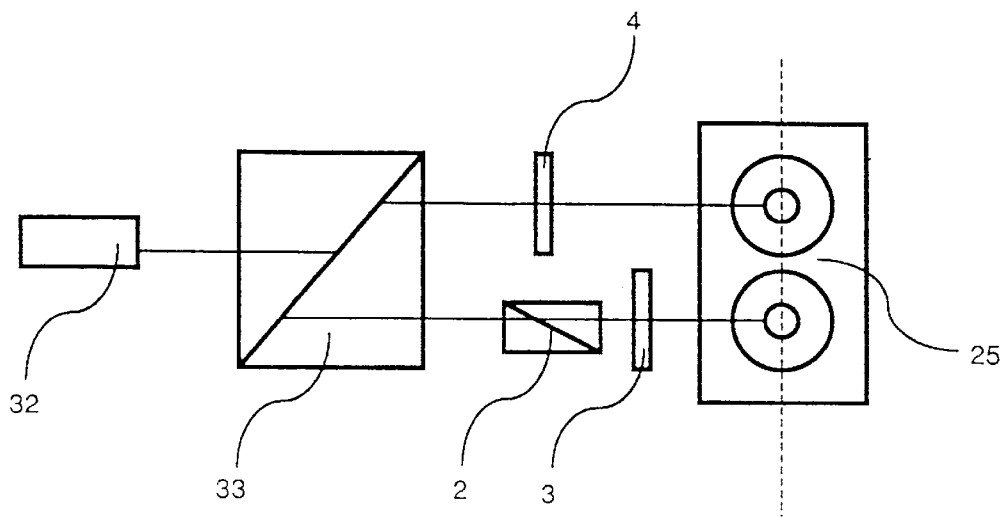
FIG. 9 shows an instrument for differential measurement of the refractive index of a fluid, using a calcite prism and a sensor according to the invention, viewed from above.

FIG. 9 depicts an instrument for differential measurement of the refractive index of a fluid using a nonpolarized coherent light source 32. A calcite separation prism 33 is used to separate the beam into two.

Figure 10:
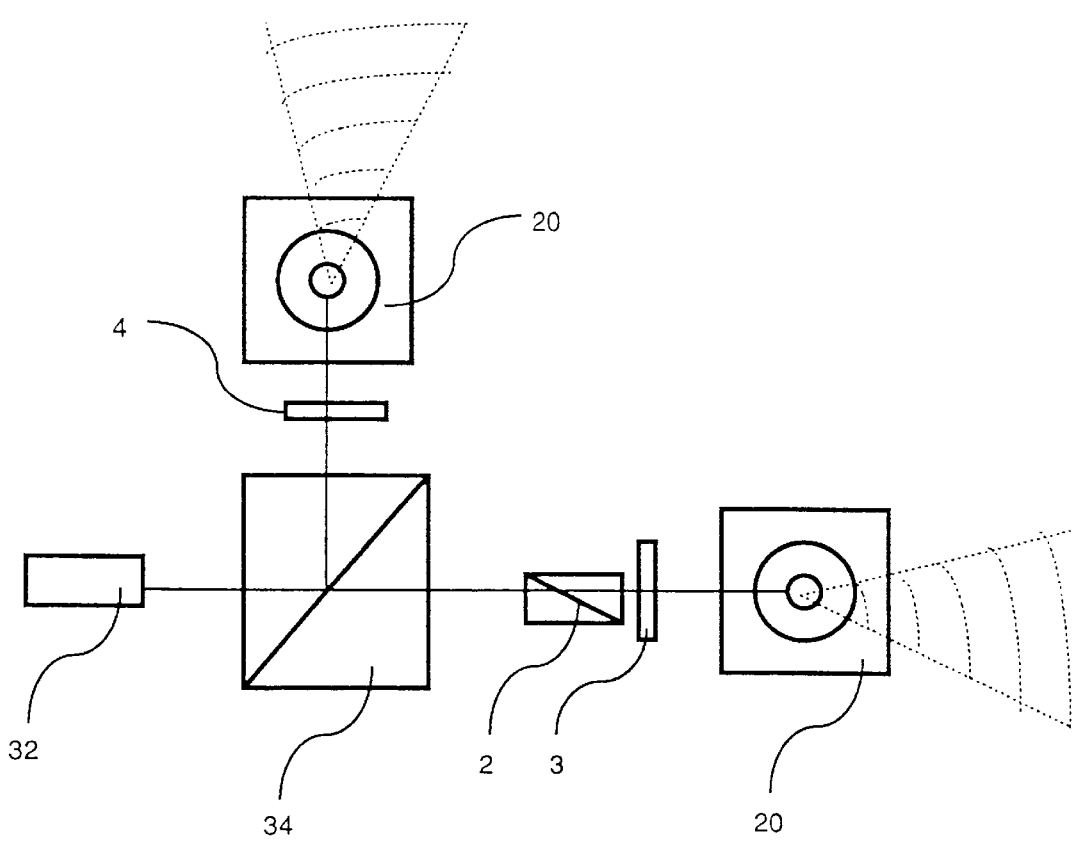
FIG. 10 shows an instrument for differential measurement of the refractive index of a fluid, using a 90-degree prism and a sensor according to the invention, viewed from above.

FIG. 10 depicts an instrument for differential measurement of the refractive index of a fluid using a nonpolarized coherent light source. A 90-degree or 45-degree separation prism 34 is used to separate the beam into two. A half-wave plate 4 is used to adjust the phase angle of one of the two beams.

The sensor 6 according to the invention can be used as a temperature sensor, salinometer, pressure meter, or densitometer, depending on how it is contained and on the processing applied to the refractive index measurements.

The principal field to which the sensor 6 relates is oceanography. It may relate, however, to other fields, especially to industries which perform density or temperature measurements on fluids in production lines. It may also relate to the medical field, particularly in terns of gas analysis. Lastly, analytical laboratories may utilize this type of sensor to characterize fluids which can circulate under pressure.

What is claimed is:

1. An instrument for measuring the refractive index of a fluid, comprising:

a coherent light source which emits at least one beam of coherent light;

a sensor that receives and contains the fluid whose refractive index is to be measured, the sensor being illuminated by the light source and comprising a block of material which is transparent to the light and includes a machined portion which comprises a hole or a groove, the sensor having a surface which is flat and parallel to the hole or the groove;

a photodetector that receives the coherent light beam that has been directly transmitted or reflected by the sensor, wherein superimposition of rays of the light beam which have traveled along different optical paths through the walls of the sensor, by transmission and/or reflection of the light beam at various optical interfaces of the sensor, leads to the formation of interference fringes, the photodetector tracking movement of the interference fringes directly from the sensor, the movement of the interference fringes being a function of changes in the refractive index of the fluid contained in the sensor; and a processor that determines the refractive index of the fluid contained in the sensor from the interference fringes tracked by the photodetector.

2. The instrument for measuring the refractive index of a fluid as defined in claim 1, wherein the shape of the sensor is a cube or a parallelepiped, the sensor having a bore over its entire length.

3. The instrument for measuring the refractive index of a fluid as defined in claim 1, wherein the shape of the sensor is a cube or a parallelepiped, the sensor being drilled out over only a portion of its length.

4. The instrument for measuring the refractive index of a fluid as defined in claim 2, wherein the sensor bore has an inlet that is machined.

5. The instrument for measuring the refractive index of a fluid as defined in claim 4, wherein the sensor bore has a conical shaped inlet.

6. The instrument for measuring the refractive index of a fluid as defined in claim 2, wherein the sensor bore has an outlet that is machined.

7. The instrument for measuring the refractive index of a fluid as defined in claim 6, wherein the sensor bore has a conical shaped outlet.

8. The instrument for measuring the refractive index of a fluid as defined in claim 5, wherein the dimensions of the conical shaped inlet causes the flow in the bore to be laminar.

9. The instrument for measuring the refractive index of a fluid as defined in claim 4, wherein a flexible pressure-tight connector is attached to the inlet and/or outlet of the sensor.

10. The instrument for measuring the refractive index of a fluid as defined in claim 1, wherein the sensor is manufactured from a material which is transparent and is selected from among materials consisting of mixtures of natural quartz or silica, synthetic quartz or silica, optical glasses of the borosilicate crown or flint type, sapphire, crystalline silicon, zinc selenide, or composite ceramic glasses.

11. The instrument for measuring the refractive index of a fluid as defined in claim 2, wherein the outer surfaces of the sensor and the wall of the bore are polished, the outer surfaces having an antireflection coating.

12. The instrument for measuring the refractive index of a fluid as defined in claim 1, wherein the coherent light source, the sensor, and the photodetector are manufactured using micro-optical technology, and are integrated onto a single substrate.

13. The instrument for measuring the refractive index of a fluid as defined in claim 1, wherein the sensor surface illuminated by the coherent light beam has an antireflection coating, and the opposite surface has a coating which absorbs the reflected beam.

14. The instrument for measuring the refractive index of a fluid as defined in claim 1, wherein the shape of the sensor is a cylinder of which the sensor surface illuminated by the coherent light beam, and the sensor surface transmitting the interference fringes, are rendered flat.

15. The instrument for measuring the refractive index of a fluid as defined in claim 1, wherein the sensor has two parallel holes containing respectively a reference fluid with a known refractive index, and a fluid whose refractive index is to be determined.

16. The instrument for measuring the refractive index of a fluid as defined in claim 1, wherein the sensor is produced from two semicylindrical or parallelepipedal half-elements, assembled by optical contact or by any other adhesion method, the bore of which has a rectangular shape.

* * * * *